United States Patent [19]

Aoki et al.

[11] 4,005,148
[45] Jan. 25, 1977

[54] DERIVATIVES OF PROPARGYL OR ALKENYL PHENYL ETHER AND USE THEREOF AS ACARICIDE

[75] Inventors: Yukio Aoki, Omiya; Shizuo Wakita; Shoichi Kato, both of Ageo; Shuichi Ishida, Omiya, all of Japan

[73] Assignee: Nippon Kayaku Kabushiki Kaisha, Tokyo, Japan

[22] Filed: Aug. 5, 1975

[21] Appl. No.: 602,069

[30] Foreign Application Priority Data

Aug. 9, 1974  Japan ............................... 49-90760

[52] U.S. Cl. .................... 260/607 AR; 424/337; 260/609 F
[51] Int. Cl.² ........................................ C07C 147/14
[58] Field of Search ................ 260/607 AR, 609 F; 424/337

[56] References Cited

FOREIGN PATENTS OR APPLICATIONS

| 7,037,147 | 7/1971 | France ........................... 260/607 A |
| 528,210 | 4/1969 | Switzerland .................... 260/607 A |
| 1,332,189 | 10/1970 | United Kingdom ........... 260/607 A |

OTHER PUBLICATIONS
J. Amer. Chem. Soc., vol. 80, pp. 3271–3276, (1958).

*Primary Examiner*—Lewis Gotts
*Assistant Examiner*—D. R. Phillips
*Attorney, Agent, or Firm*—Russell & Nields

[57] ABSTRACT

A new compound of the formula

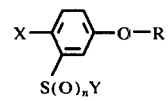

wherein X represents methyl group or chlorine atom, Y represents a lower alkyl group having from 1 to 6 carbon atoms or allyl group, R represents propargyl group or an alkenyl group having from 3 to 18 carbon atoms, which may be substituted by chlorine atom and $n$ represents 0, 1 or 2 is used for combating acarids.

3 Claims, No Drawings

DERIVATIVES OF PROPARGYL OR ALKENYL PHENYL ETHER AND USE THEREOF AS ACARICIDE

BACKGROUND OF THE INVENTION

It is well known in the art that the two-spotted spider mite or *Tetranychus urticae* inflicts great and heavy damages on agriculturally important fruits such as apple, pear, peach, etc., vegetables such as egg-plant, cucumber, etc., various kinds of beans, hop, mulberry, carnation, etc., and the citrus red mite or *Panonychus citri* also causes serious damage to citrus fruits, pear, apple, peach, mulberry, etc. In order to remove or prevent the mite infection of the crops or fruits, a variety of acaricides have heretofore been used. However, the mites tend to have a resistance to most of the known acaricides and therefore the known acaricides have not been efficient in clearing up infections of these mites.

SUMMARY OF THE INVENTION

It is therefore an object of the present invention to provide a new derivatives of propargyl or alkenyl phenyl ether having acaricidal activity and a method of preparing thereof.

It is another object of the present invention to provide a new method of combating acarids and a new acaricidal composition.

The new derivatives are represented by the formula

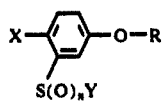
(I)

wherein X represents methyl group or chlorine atom, Y represents a lower alkyl group having from 1 to 6 carbon atoms or allyl group, R represents propargyl group or an alkenyl group having from 3 to 18 carbon atoms, which may be substituted by chlorine atom and $n$ represents 0, 1 or 2.

The new derivatives are prepared by condensing in the presence of an alkaline compound a compound of the formula

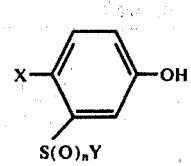
(II)

wherein X, Y and $n$ have the same meaning as defined above, with equivalent of a compound of the formula $$Z - R \quad (III)$$

wherein Z represents a halogen atom and R has the same meaning as defined above, or condensing an alkali metal salt of a compound of the formula (II) with a compound of the formula (III).

A method for combating acarids of the present invention comprises applying to acarids and their eggs an effective amount of a compound of the formula (I).

An acaricidal composition of the present invention comprise 0.5—70% by weight of a compound of the formula (I) and 95.5–30% by weight of suitable adjuvants.

An ajuvant mentioned herein means an additive which does not have acaricidal activity. The additive may include a carrier or a supplementary material which is usually employed in agricultural chemicals.

The carrier may be a solid, liquid or gas. That is to say, the solid carrier may be, for example, a clay, talc, bentonite, white carbon, kaolin, diatomaceous earth or silica. The liquid carrier may be, for example, water, benzene, kerosene, alcohols, acetone, xylene, methylnaphthalene, cyclohexane, animal and plant oils, aliphatic acids or esters of aliphatic acids, and the gaseous carrier may be air, nitrogen, carbon dioxide, fleon or the like.

The supplementary material includes, for example, a spreader, a surfactant, a sticking agent, a wetting or surface active agent, viz, polyoxyethylenealkylallylether, polyvinyl alcohol, polyoxy-ethylenesorbitanmonooleate, alkyldimethylbenzylammoniumchloride, alkylbenzenesulfonate, ligninsulfonate, an ester of higher alcohol and sulfuric acid, etc.

DESCRIPTION OF THE INVENTION

Compounds of the formula (I) are specifically shown in Table 1.

Table 1

| Compound No. | X | Y | R | n | $n_D^{25}$ or m.p. (° C) | Appearance |
|---|---|---|---|---|---|---|
| 1 | CH₃ | C₃H₇(n) | —CH₂CH=CH₂ | 0 | $n_D^{25}$ 1.5506 | Colorless oil |
| 2 | CH₃ | C₃H₇(n) | —CH₂CH=CH₂ | 1 | $n_D^{25}$ 1.5488 | " |
| 3 | CH₃ | C₃H₇(n) | —CH₂C≡CH | 0 | $n_D^{25}$ 1.5593 | Pale yellow oil |
| 4 | CH₃ | C₃H₇(n) | —CH₂C≡CH | 1 | $n_D^{25}$ 1.5561 | Colorless oil |
| 5 | CH₃ | C₃H₇(n) | —CH₂CH=CHCl | 0 | $n_D^{25}$ 1.5645 | " |
| 6 | CH₃ | C₃H₇(n) | —CH₂CH=CHCl | 1 | $n_D^{25}$ 1.5608 | Pale yellow oil |
| 7 | CH₃ | C₃H₇(n) | —CH₂CH=CHCH₃ | 0 | $n_D^{25}$ 1.5500 | Colorless oil |
| 8 | CH₃ | C₃H₇(n) | —CH₂CH=CHCH₃ | 1 | $n_D^{25}$ 1.5468 | " |
| 9 | CH₃ | C₃H₇(n) | CH₃<br>\|<br>—CH—CH=CH₂ | 0 | $n_D^{25}$ 1.5420 | " |
| 10 | CH₃ | C₃H₇(n) | CH₃<br>\|<br>—CH—CH=CH₂ | 1 | $n_D^{25}$ 1.5395 | " |

Table 1-continued

| Compound No. | X | Y | R | n | $n_D^{25}$ or m.p. (°C) | Appearance |
|---|---|---|---|---|---|---|
| 11 | CH₃ | C₃H₇(n) | —CH₂C(CH₃)=CH₂ | 0 | $n_D^{25}$ 1.5435 | " |
| 12 | CH₃ | C₃H₇(n) | " | 1 | $n_D^{25}$ 1.5407 | " |
| 13 | CH₃ | C₃H₇(n) | " | 2 | $n_D^{25}$ 1.5280 | " |
| 14 | CH₃ | C₃H₇(n) | —CH₂CH=C(CH₃)(CH₃) | 0 | $n_D^{25}$ 1.5488 | Pale yellow oil |
| 15 | CH₃ | C₃H₇(n) | " | 1 | $n_D^{25}$ 1.5458 | " |
| 16 | CH₃ | C₃H₇(n) | —(CH₂)₈CH=CH(CH₂)₇CH₃ | 1 | $n_D^{25}$ 1.5070 | Colorless oil |
| 17 | CH₃ | C₃H₇(i) | —CH₂CH=C(Cl)(CH₃) | 0 | $n_D^{25}$ 1.5535 | " |
| 18 | CH₃ | C₃H₇(i) | " | 1 | m.p. 80–83° C. | White crystals |
| 19 | CH₃ | C₄H₉(n) | —CH₂C(CH₃)—CH₂ | 0 | $n_D^{25}$ 1.5378 | Colorless Oil |
| 20 | CH₃ | C₄H₉(n) | " | 1 | $n_D^{25}$ 1.5406 | " |
| 21 | CH₃ | CH₂CH=CH₂ | —CH₂CH=CHCH₃ | 0 | $n_D^{25}$ 1.5645 | Pale yellow oil |
| 22 | Cl | CH₃ | —CH₂CH—CHCH₃ | 0 | m.p. 36–37° C | White crystals |
| 23 | Cl | CH₃ | —CH₂CH=CHCH₃ | 1 | $n_D^{25}$ 1.5718 | Pale yellow oil |
| 24 | Cl | C₂H₅ | —CH₂CH=CHCl | 0 | $n_D^{25}$ 1.5872 | Colorless oil |
| 25 | Cl | C₃H₇(n) | —CH₂CH=CH₂ | 0 | $n_D^{25}$ 1.5679 | " |
| 26 | Cl | C₃H₇(n) | —CH₂CH=CH₂ | 1 | $n_D^{25}$ 1.5590 | " |
| 27 | Cl | C₃H₇(n) | —CH₂C≡CH | 0 | $n_D^{25}$ 1.5760 | Pale yellow oil |
| 28 | Cl | C₃H₇(n) | —CH₂C≡CH | 1 | $n_D^{25}$ 1.5710 | Yellow oil |
| 29 | Cl | C₄H₉(n) | —CH(CH₃)—CH=CH₂ | 0 | $n_D^{25}$ 1.5498 | Colorless oil |
| 30 | Cl | C₄H₉(n) | —CH(CH₃)—CH=CH₂ | 1 | $n_D^{25}$ 1.5439 | Colorless oil |
| 31 | CH₃ | C₃H₇(n) | —CH₂CH=O—CH₃ CH₂CH₂CH=C(CH₃)(CH₃) | 0 | $n_D^{25}$ 1.5386 | Pale yellow oil |
| 32 | CH₃ | C₃H₇(n) | " | 1 | $n_D^{25}$ 1.5393 | Colorless oil |
| 33 | Cl | C₃H₇(n) | " | 0 | $n_D^{25}$ 1.5476 | " |
| 34 | Cl | C₃H₇(n) | " | 1 | $n_D^{25}$ 1.5425 | " |
| 35 | CH₃ | C₃H₇(n) | —(CH₂)₈CH=CH(CH₂)₇CH₃ | 0 | $n_D^{25}$ 1.5063 | " |
| 36 | CH₃ | C₃H₇(n) | —CH₂CH=CHCH₃ | 2 | $n_D^{25}$ 1.5346 | " |
| 37 | CH₃ | C₃H₇(n) | —CH₂CH=CH₂ | 2 | $n_D^{25}$ 1.5359 | " |
| 38 | CH₃ | C₃H₇(n) | —CH₂O≡CH | 2 | $n_D^{25}$ 1.5410 | " |

The preferable compounds as an acaricids are the compounds of the formula (I) where X represents methyl group or chlorine atom, Y represents ethyl group, n-propyl group or allyl group, R represents propargyl group, allyl group, buten-2-yl group, 3-methylbuten-2-yl group, 1-methylallyl group or 3-chloroallyl group and n represents 0 or 1. The most preferable compounds as an acaricide are the compounds of the formula (I) where X represents methyl group or chlorine atom, Y represents n-propyl group, R represents propargyl group, allyl group, 3-chloroallyl group or buten-2-yl group and n represents 0 or 1.

The most preferable compounds are, for example, compounds No. 1, No.2, No.3, No.4, No.5, No.6, No.8, No.14, No.24, No.25, No.26, No.27 and No.28.

The condensation of a compound of the formula (II) with equivalent of a compound of the formula (III) in the presence of an alkaline compound or an alkali metal salt of a compound of the formula (II) with equivalent of a compound of the formula (III) is usually condusted in an inert solvent such as N,N-dimethylacetamide (DMAC), di-methyl sulfoxide (DMSO), dimethylformamide (DMF), methanol, ethanol, benzene, aceton and water preferably DMAC, DMSO and DMF but may be conducted in an absence of the solvent.

The reaction temperature is in the range of 0° C – 160° C preferably 10° – 120° C. The alkaline compounds are, for example, alkali methal hydroxides such as sodium hydroxide and potassium hydroxide and alkali metal carbonates such as potassium carbonate and sodium carbonate.

The alkali metal salts of a compound of the formula (II) are for example, sodium salt and potassium salt.

When a compound of the formula (I) is a sulfide, the compound may be oxidized by a oxidizing agent such as hydrogen peroxide, potassium permanganate, potassium persulfate, perbenzoic acid and nitric acid to obtain a corresponding sulfoxide or a corresponding sulfone.

In order to exterminate an acarid, an effective amount of a compound of the formula (I) for acaricide is applied to acarids.

The acaricidal compositions of the present invention are, for example, an emulsifiable concentrate, a wettable powder, a dusting powder or a granule. The emulsifiable concentrate or the wettable powder comprises 5–70% by weight, preferably 10–50% by weight of a compound of the formula (I) and 95–30% by weight, preferably 90–50% by weight of adjuvants.

The emulsifiable concentrate or the wettable powder is diluted with water to obtain a emulsion or a solution in which the concentration of a compound of the formula (I) is 0.1–0.01% by weight and the emulsion or the solution is sprayed in an amount of 100–1000 liter/10 ares. The dusting powder or the granule comprises 0.5—10% by weight of a compound of the formula (I) and 95.5–90% by weight of suitable adjuvants and is usually scattered in an amount of 1–5 kg/10 ares.

The acaricidal composition may be used in combination with other agricultural chemicals such as a pesticide, a herbicide, a fungicide or an acaricide.

The following are some examples of the preparation of compounds of the formula (I), some examples of the composition of the present invention and some examples which exhibit an excellent acaricidal effect of the present invention. All parts are by weight.

EXAMPLE 1

The preparation of 3-chloro-propen-2-yl 4'-chloro-3'-ethylthiophenyl ether (Compound No.24).

Six (6) g of 4-chloro-3-ethylthiophenol and 2.1 g of potassium hydroxide (purity=85.5%) were disolved in 30 ml of DMAC above 90° C.

After the solution was cooled at 18°–28° C, 3.5g of 3-chloropropen-2-ylchloride were added to the solution and then the mixture was stirred for 3 hours at 70°–80° C. The reaction mixture was poured into 100 ml of water and extracted with benzene. The extract was washed with a 5% hydrochloric acid solution and a 5% sodium hydroxide solution.

After thus washed extract dried over sodium sulfate, benzene was removed by distillation to obtain 67 g (80.1% of the theoritical yield) of 3-chloro-propen-2-yl 4'-chloro-3'-ethylthiophenyl ether.

Elemental analysis for $C_{11}H_{12}Cl_2OS$: Found: C, 50.08; H, 4.60%. Calculated: C, 50.16; H, 4.56%.

In this Example, potassium salt of 4-chloro 3-ethylthiophenol instead of 4-chloro-3-ethylthiophenol and potassium hydroxide was used and the similar method was repeated. 3-chloro-propen-2-yl-4'-chloro-3'-ethylthiophenylether could be obtained.

EXAMPLE 2

The compounds shown in Table 2 were prepared by the similar method to Example 1.

Table 2

| Compound No. | X | Y (M:H or alkaline metal atom) | M | n | Z | Z – R | R | Solvent | Reaction Temperature (°C) | Time (hr) | Alkaline compound (when M represent atom) | Yield (%) |
|---|---|---|---|---|---|---|---|---|---|---|---|---|
| 1 | $CH_3$ | $-C_3H_7(n)$ | K | O | Br | | $-CH_2CH=CH_2$ | DMF | 18–28 | 5 | | 87.5 |
| 3 | $CH_3$ | $-C_3H_7(n)$ | K | O | Br | | $-CH_2C\equiv CH$ | " | 18–28 | 3.5 | | 73.0 |
| 5 | $CH_3$ | $-C_3H_7(n)$ | H | O | Cl | | $-CH_2CH=CHCl$ | " | 70–80 | 3 | $K_2CO_3$ | 84.4 |
| 7 | $CH_3$ | $-C_3H_7(n)$ | K | O | Cl | | $-CH_2CH=CHCH_3$ | " | 18–28 | 6 | | 81.8 |
| 9 | $CH_3$ | $-C_3H_7(n)$ | Na | O | Cl | | $-CHCH=CH_2$ <br> $\quad\ \|$ <br> $\quad CH_3$ | DMAC | 18–28 | 4.5 | | 70.8 |
| 11 | $CH_3$ | $-C_3H_7(n)$ | Na | O | Cl | | $-CH_2-C\equiv CH_2$ <br> $\qquad\ \|$ <br> $\qquad CH_3$ | " | 18–28 | 6 | | 76.4 |
| 14 | $CH_3$ | $-C_3H_7(n)$ | K | O | Cl | | $-CH_2CH=C-CH_3$ <br> $\qquad\qquad \|$ <br> $\qquad\qquad CH_3$ | " | 25–35 | 5 | | 83.0 |
| 17 | $CH_3$ | $-C_3H_7(i)$ | K | O | Cl | | $-CH_2CH=C-Cl$ <br> $\qquad\qquad \|$ <br> $\qquad\qquad CH_3$ | DMF | 50–60 | 5 | | 74.1 |
| 19 | $CH_3$ | $-C_4H_9(n)$ | K | O | Cl | | $-CH_2C\equiv CH_2$ <br> $\qquad \|$ <br> $\qquad CH_3$ | " | 85–95 | 6 | | 86.1 |
| 21 | $CH_3$ | $-CH_2CH=CH_2$ | K | O | Cl | | $-CH_2CH=CHCH_3$ | " | 18–28 | 8 | | 92.2 |
| 22 | Cl | $-CH_3$ | K | O | Cl | | $-CH_2CH=CHCH_3$ | DMF | 75–85 | 4 | | 91.6 |
| 25 | Cl | $-C_3H_7(n)$ | Na | O | Cl | | $-CH_2CH=CH_2$ | " | 55–65 | 3 | | 95.5 |
| 27 | Cl | $-C_3H_7(n)$ | K | O | Br | | $-CH_2C\equiv CH$ | " | 60–70 | 2 | | 98.1 |
| 29 | Cl | $-C_4H_9(n)$ | K | O | Cl | | $CH_3$ <br> $\ \|$ <br> $-CHCH=CH_2$ | DMF | 65–75 | 5 | | 84.3 |
| 31 | $CH_3$ | $-C_3H_7(n)$ | K | O | Br | | $-CH_2CH=CCH_2CH_2CH=C-CH_3$ <br> $\qquad\qquad\ \|\qquad\qquad\quad \|$ <br> $\qquad\qquad CH_3\qquad\qquad\ CH_3$ | DMAC | 18–28 | 6 | | 90.6 |
| 33 | Cl | $-C_3H_7(n)$ | K | O | Br | | " | DMF | 18–28 | 8 | | 74.1 |

Table 2-continued

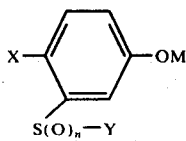

| Compound No. | (M:H or alkaline metal atom) X | Y | M | n | Z | Z – R R | Solvent | Reaction Temperature (°C) | Time (hr) | Alkaline compound (when M represent atom) | Yield (%) |
|---|---|---|---|---|---|---|---|---|---|---|---|
| 35 | CH₃ | —C₃H₇(n) | K | O | Cl | —(CH₂)₈CH=CH(CH₂)₇CH₃ | " | 85–95 | 2.5 | | 85.8 |

EXAMPLE 3

The preparation of 3-chloro-buten-2-yl 4'-methyl-3'-i-propylsulfinylphenyl ether (Compound No.18)

Two (2) g of 4-methyl-3-i-propylsulfinylphenol, 1.4 g of potassium carbonate, 30 ml of DMAC and 1.3 g of 3-chloro-buten-2-yl chloride were mixed and reacted at 90°–100° C for 5 hours. The resultant reaction mixture was poured into 100 ml of water and extracted with benzene. The extract was washed with 5% sodium hydroxide solution and water. After the washed extract was dried over sodium sulfate, the benzene was removed by distillation to obtain 2 g (71.2% of the theoretical yield) of 3-chloro-buten-2-yl 4'-methyl-3'-i-propylsulfinyl-phenyl ether.

Elemental analysis for C₁₄H₁₉ClO₂S: Found: C, 58.49; H, 6.78%. Calculated: C, 8.64; H, 6.63%.

The compounds No.2, No.4, No.6, No.8, No.10, No.12, No.15, No.16, No.20, No.23, No.26, No.28, No.30, No.32 and No.34 can be prepared by the similar method to this Example.

EXAMPLE 4

The preparation of allyl 4-methyl-3-n-propylsulfinylphenyl ether (Compound No.2)

Three (3.0) g of allyl 4-methyl-3-n-propylthiophenyl ether (Compound No.1) were dissolved into 30 ml of acetic acid. The resultant solution was cooled below 5° C and 2.5 g of 30% hydrogen peroxide solution were added to the solution. After the solution stirred at room temperature for 1 hour, the reaction mixture was poured into 100 ml of water and extracted with benzene. The obtained extract was washed with 5% sodium carbonate solution and then water and dried over sodium sulfate.

Then, benzene was removed to obtain 3.1 g (96.3% of the theoritical yield) of allyl 4-methyl-3-n-propylsulfinyl-phenyl ether.

Elemental analysis for C₁₃H₁₈O₂S: Found: C, 70.11%; H, 8.13%. Calculated: C, 70.16%; H, 8.10%.

The compounds No.4, No.6, No.8, No.10, No.12, No.15, No.16, No.20, No.23, No.26, No.28, No.30, No.32 and No.34 were prepared by oxidation of the corresponding sulfide by the similar method to this Example.

EXAMPLE 5

The preparation of 2-methyl-propen-2-yl 4'-methyl-3'-n-propylsulfonylphenyl ether (Compound No. 13)

Five (5) g of 2-methyl-propen-2-yl 4'-methyl-3'-n-propyl-thiophenyl ether (Compound No.11) were disloved into 30 ml of acetic acid. After the solution was cooled below 5° C, 6.2g of 30% hydrogen peroxide solution were added dropwise to the solution and then the solution was stirred at 80° C for 3 hours. The reaction mixture was poured into 100 ml of water and extracted with ether. The resultant extract was washed with 5% sodium hydrogen-carbonate solution and water. After the washed extract was dried over sodium sulfate, the ether was removed by distillation to obtain 4.46g (78.4% of the theoretical yield) of 2-methyl-propen-2-yl 4'-methyl-3'-n-propyl-sulfonylphenyl ether.

Elemental analysis for C₁₄H₂₀O₃S: Found: C, 62.51; H, 7.53%. Calculated: C, 62.60; H, 7.45%.

EXAMPLE 6

Emulsifiable concentrate

| | |
|---|---|
| Compound No. 3 | 20 parts |
| Xylene | 65 parts |
| The mixture of calcium alkylbenzensulfonate and a condensation product of an alkylphenol and ethylenoxide | 15 parts |

The above ingredients were blended to obtain an emulsifiable concentrate which was diluted with water for spraying.

EXAMPLE 7

Wettable powder

| | |
|---|---|
| Compound No. 8 | 30 parts |
| Caoline | 40 parts |
| Clay | 15 parts |
| Diatomaceous earth | 7.5 parts |
| A mixture of sodium laurate and dinaphthylmethane sulfonic acid | 7.5 parts |

The above ingredients were blended to form a wettable powder which is diluted with water for use.

EXAMPLE 8

Dusting powder

| | |
|---|---|
| Compound No. 26 | 3 parts |
| Talc | 48 parts |
| Clay | 49 parts |

The above ingredients were mixed and crushed to form fine powder which was applied as it is for use.

EXAMPLE 9

Two seed leaves of a kidney-bean which was cultivated in porous pot having a diameter of 6 cm. were cut into pieces of about 3 square cm. Fifteen female imagos of the two-spotted spider mite were inoculated per leaf. Then, each leaf was immersed for 10 seconds in a solution containing 0.043% by weight of an acaricidal compound of the present invention. The resultant leaves were allowed to stand for 48 hours in a green house. The death and life of the mites were observed to calculate an acaricidal ratio. Thereafter, living mites were removed from each of the leaves. After leaving the leaves in the green house for 7 days, the number of unhatched eggs were examined. The results were shown in Table 3.

Table 3

| Compound No. | Acaricidal ratio (%) | Egg-killing ratio (%) |
|---|---|---|
| 1 | 100 | 100 |
| 2 | 100 | 100 |
| 3 | 100 | 100 |
| 4 | 100 | 100 |
| 5 | 100 | 100 |
| 6 | 100 | 100 |
| 7 | 100 | 82 |
| 8 | 100 | 100 |
| 9 | 100 | 96 |
| 10 | 100 | 88 |
| 11 | 93 | 73 |
| 12 | 72 | 91 |
| 13 | 88 | 72 |
| 14 | 100 | 100 |
| 15 | 86 | 100 |
| 16 | 100 | 77 |
| 17 | 69 | 92 |
| 18 | 63 | 93 |
| 19 | 98 | 82 |
| 20 | 95 | 67 |
| 21 | 100 | 100 |
| 22 | 85 | 100 |
| 23 | 65 | 73 |
| 24 | 100 | 100 |
| 25 | 100 | 100 |
| 26 | 100 | 100 |
| 27 | 100 | 100 |
| 28 | 100 | 100 |
| 29 | 64 | 98 |
| 30 | 80 | 70 |
| 31 | 78 | 63 |
| 32 | 64 | 98 |
| 33 | 64 | 75 |
| 34 | 69 | 99 |
| 35 | 78 | 66 |
| 36 | 76 | 62 |
| 37 | 79 | 63 |
| 38 | 72 | 62 |
| No-treated | 3 | 0 |

EXAMPLE 10

A summer orange was cultivated in a porous pot having a diameter of 12 cm. All leaves except two were cut off. An adhesive material was applied onto the stalks of two leaves for prevention of escape of mites and 10 female imagos of citrus red mites were inoculated per leaf and allowed to deposit eggs for 2 days in a green house. Then, a solution containing 0.04% by weight of compounds in accordance with the present invention were scattered on each leaf for 10 seconds by means of a spray gun. After the scattering, the resultant leaves were allowed to stand for 2 days in a green house. The death and life of the mites were observed by means of a binocular stereomicroscope to calculate an acaricidal ratio.

Thereafter, the dead and living mites were removed from each of the leaves and the numbers of eggs were counted, leaving in the leaves in the green house for 7 days. Numbers of unhatched eggs were observed by means of a binocular stereomicroscope to obtain the egg-killing ratio.

The test results are shown in Table 4.

Table 4

| Compound No. | Acaricidal ratio (%) | Egg-killing ratio (%) |
|---|---|---|
| 1 | 100 | 96 |
| 2 | 100 | 100 |
| 3 | 96 | 91 |
| 4 | 100 | 100 |
| 5 | 85 | 72 |
| 6 | 100 | 100 |
| 8 | 100 | 100 |
| 24 | 90 | 73 |
| 25 | 96 | 67 |
| 26 | 100 | 100 |
| 27 | 100 | 100 |
| No-treated | 3 | 0 |

We claim:

1. A compound represented by the formula:

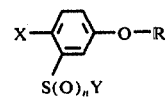

(1)

wherein X represents methyl group or chlorine atom, Y represents ethyl group, n-propyl group, or allyl group, R represents propargyl group, allyl group, buten-2-yl group, 3-methyl buten-2-yl group, 1-methylallyl group, 3-chloroallyl group, and $n$ represents 0 or 1.

2. A compound according to claim 1 wherein X represents methyl group, Y represents n-propyl group, and R represents allyl group.

3. A compound according to claim 1 wherein X represents methyl group or chlorine atom, Y represents n-propyl group, R represents propargyl group, allyl group, 3-chloroallyl group or buten-2-yl group and $n$ represents 0 or 1.

* * * * *